(12) United States Patent
Moran et al.

(10) Patent No.: US 7,629,027 B2
(45) Date of Patent: Dec. 8, 2009

(54) METHOD FOR MAKING CHROMONIC NANOPARTICLES

(75) Inventors: Cristin E. Moran, Woodbury, MN (US); Hassan Sahouani, Hastings, MN (US); Larry D. Boardman, Woodbury, MN (US); Sanat Mohanty, Minneapolis, MN (US)

(73) Assignee: 3M Innovative Properties Company, Saint Paul, MN (US)

( * ) Notice: Subject to any disclaimer, the term of this patent is extended or adjusted under 35 U.S.C. 154(b) by 812 days.

(21) Appl. No.: 11/250,290

(22) Filed: Oct. 14, 2005

(65) Prior Publication Data

US 2007/0086964 A1    Apr. 19, 2007

(51) Int. Cl.
*B05D 5/00* (2006.01)
(52) U.S. Cl. .................. 427/256; 428/1.1; 428/1.2; 428/1.31; 252/299.4; 252/299.5; 252/299.1; 427/212
(58) Field of Classification Search .................. 428/1.1, 428/1.31; 252/299.1, 585; 427/212, 256
See application file for complete search history.

(56) References Cited

U.S. PATENT DOCUMENTS

| | | | |
|---|---|---|---|
| 4,689,338 A | 8/1987 | Gerster | |
| 4,882,166 A | 11/1989 | Graham et al. | |
| 4,929,624 A | 5/1990 | Gerster et al. | |
| 4,988,815 A | 1/1991 | André et al. | |
| 5,037,986 A | 8/1991 | Gerster | |
| 5,175,296 A | 12/1992 | Gerster | |
| 5,837,275 A | 11/1998 | Burrell et al. | |
| 5,876,682 A | 3/1999 | Kurihara et al. | |
| 5,948,487 A | 9/1999 | Sahouani et al. | |
| 6,051,290 A | 4/2000 | Sahouani et al. | |
| 6,069,149 A | 5/2000 | Nanba et al. | |
| 6,214,499 B1 | 4/2001 | Helber et al. | |
| 6,245,399 B1 * | 6/2001 | Sahouani et al. | 428/1.31 |
| 6,248,364 B1 | 6/2001 | Sengupta et al. | |
| 6,344,272 B1 | 2/2002 | Oldenburg et al. | |
| 6,355,386 B1 | 3/2002 | Helber et al. | |
| 6,395,354 B1 | 5/2002 | Sahouani et al. | |
| 6,411,354 B1 | 6/2002 | Lavrentovich et al. | |
| 6,488,866 B1 | 12/2002 | Sahouani et al. | |
| 6,527,977 B2 | 3/2003 | Helber et al. | |
| 6,538,714 B1 | 3/2003 | Sahouani et al. | |

(Continued)

FOREIGN PATENT DOCUMENTS

EP    1 232 414 B1    2/2004

(Continued)

OTHER PUBLICATIONS

Fang et al., "Aggregation and Surface-Enhanced Raman Activity Study of Dye-Coated Mixed Silver-Gold Colloids", Journal of Raman Spectroscopy, (2004), pp. 914-920, vol. 35, No. 11, John Wiley & Sons, Ltd.

(Continued)

*Primary Examiner*—Michael Kornakov
*Assistant Examiner*—Andrew Bowman
(74) *Attorney, Agent, or Firm*—Gregory D. Allen

(57) ABSTRACT

A chromonic nanoparticle mixture prepared by combining (i) a continuous water-soluble polymer phase and (ii) a discontinuous chromonic phase comprising a chromonic material; and non-covalently crosslinking the resulting chromonic nanoparticles with a polyvalent cation salt.

30 Claims, 2 Drawing Sheets

U.S. PATENT DOCUMENTS

| | | | |
|---|---|---|---|
| 6,562,363 | B1 | 5/2003 | Mantelle et al. |
| 6,570,632 | B2 | 5/2003 | Lavrentovich et al. |
| 6,574,044 | B1 | 6/2003 | Sahouani et al. |
| 6,576,712 | B2 | 6/2003 | Feldstein et al. |
| 6,645,578 | B2 * | 11/2003 | Sahouani et al. ............ 428/1.2 |
| 6,673,398 | B2 | 1/2004 | Schneider et al. |
| 6,696,077 | B2 | 2/2004 | Scherr |
| 6,699,533 | B2 | 3/2004 | Sahouani et al. |
| 6,777,036 | B2 | 8/2004 | Bravo Vasquez et al. |
| 6,962,734 | B2 | 11/2005 | Nazarov et al. |
| 2002/0055517 | A1 | 5/2002 | Smith |
| 2002/0066885 | A1 | 6/2002 | Sahouani et al. |
| 2002/0132065 | A1 | 9/2002 | Sahouani et al. |
| 2002/0168511 | A1 | 11/2002 | Schneider et al. |
| 2003/0008145 | A1 | 1/2003 | Goldstein |
| 2003/0071243 | A1 | 4/2003 | Sahouani et al. |
| 2003/0147043 | A1 | 8/2003 | Sahouani et al. |
| 2004/0058091 | A1 * | 3/2004 | Dutova et al. ............ 428/1.1 |
| 2004/0242729 | A1 | 12/2004 | Baran, Jr. et al. |
| 2005/0123621 | A1 | 6/2005 | Burton et al. |
| 2005/0124724 | A1 | 6/2005 | Burton et al. |
| 2006/0035039 | A1 | 2/2006 | Ylitalo et al. |
| 2006/0110528 | A1 | 5/2006 | Sahouani |
| 2006/0110540 | A1 | 5/2006 | Sahouani |
| 2006/0110922 | A1 | 5/2006 | Sahouani |
| 2006/0111482 | A1 | 5/2006 | Sahouani |
| 2007/0086964 | A1 | 4/2007 | Moran et al. |
| 2007/0086965 | A1 | 4/2007 | Mohanty et al. |
| 2007/0128291 | A1 | 6/2007 | Tokie et al. |
| 2007/0140957 | A1 | 6/2007 | Mohanty et al. |
| 2007/0141351 | A1 | 6/2007 | Mohanty et al. |
| 2007/0148458 | A1 | 6/2007 | Sahouani et al. |

FOREIGN PATENT DOCUMENTS

| | | |
|---|---|---|
| KR | 10-2003-0010846 | 2/2003 |
| KR | 10-2005-0023294 | 3/2005 |
| WO | WO 98/37997 A2 | 9/1998 |
| WO | WO 00/22463 A1 | 4/2000 |
| WO | WO 01/80920 A2 | 11/2001 |
| WO | WO 02/18003 A1 | 3/2002 |
| WO | WO 2004/033488 A2 | 4/2004 |
| WO | WO 2005/011629 A1 | 2/2005 |
| WO | WO 2005/012488 A2 | 2/2005 |
| WO | WO 2006/020584 A2 | 2/2006 |

OTHER PUBLICATIONS

Stenzel et al., "The Incorporation of Metal Clusters Into Thin Organic Dye Layers as a Method for Producing Strongly Absorbing Composite Layes: An Oscillator Model Approach to Resonant Metal Cluster Absorption", Journal of Physics D: Applied Physics, (1995), pp. 2154-2162, vol. 28, No. 10, IOP Publishing, Ltd.

Attwood et al., "Lyotropic Mesophase Formation by Anti-Asthmatic Drugs", Mol. Cryst. Liq. Cryst., (1984), pp. 349-357, vol. 108.

Brinker et al., "Review of Sol-Gel Thin Film Formation", Journal of Non-Crystalline Solids, (1992), pp. 424-436, vol. 147&148, Elsevier Science Publishers B.V.

Kawasaki et al., "Controlled Layering of Two-Dimensional J-Aggregate of Anionic Cyanine Dye on Self-Assembled Cysteamine Monolayer on Au(111)", Langmuir, (2000), pp. 5409-5417, vol. 16, No. 12, American Chemical Society.

Lydon, "Chromonic Mesophases", Current Opinion in Colloid and Interface Science, (2004), pp. 480-490, vol. 8, Elsevier Ltd.

Lydon, "Chapter XVIII, Chromonics", Handbook of Liquid Crystals, (1998), pp. 981-1007, vol. 2 B: Low Molecular Weight Liquid Crystals II, Wiley-VCH Verlag GmbH, D-60469, Weinheim.

Lansdown, "Silver 1: Its Antibacterial Properties and Mechanism of Action", Journal of Wound Care, (Apr. 2002), pp. 125-130, vol. 11, No. 4.

Lansdown, "Silver 2: Toxicity in Mammals and How its Products Aid Wound Repair", Journal of Wound Care, (May 2002), pp. 173-177, vol. 11, No. 5.

Pardavi-Horvath, "Iron-Alumina Nanocomposites Prepared by Ball Milling", IEEE Transactions on Magnetics, (Sep. 1992), pp. 3186-3188, vol. 28, No. 5.

Wright et al., "Wound Management in an Era of Increasing Bacterial Antibiotic Resistance: A Role for Topical Silver Treatment", AJIC, (Dec. 1998), pp. 572-577, vol. 26, No. 6, Association for Professionals in Infection Control and Epidemiology, Inc.

U.S. Appl. No. 11/275,070, "Method and Apparatus for Forming Chromonic Nanoparticles", filed Dec. 7, 2005.

U.S. Appl. No. 11/275,075, entitled "Silver Ion Releasing Articles and Methods of Manufacture", filed Dec. 8, 2005.

U.S. Appl. No. 11/250,675, entitled Chromonic Nanoparticles Containing Bioactive Compounds, filed Oct. 14, 2005.

U.S. Appl. No. 11/275,200, entitled "Hierarchical Chromonic Structures", filed Dec. 19, 2005.

U.S. Appl. No. 11/275,202, entitled "Multilayer Chromonic Structures", filed Dec. 19, 2005.

U.S. Appl. No. 11/275,364, entitled "Encapsulated Chromonic Particles", filed Dec. 28, 2005.

U.S. Appl. No. 11/279,601, "Method and Apparatus for Forming Crosslinked Chromonic Nanoparticles", filed Apr. 13, 2006.

U.S. Appl. No. 11/419,880, "Method of Making Ordered Nanostructured Layers", filed May 23, 2006.

Aguirre, et al., "CTAB Mediated Reshaping of Metallodielectric Nanoparticles", Nano Letters, (2003), pp. 1707-1711, vol. 3, No. 12, American Chemical Society.

Barbic et al., "Single Crystal Silver Nanowires Prepared by the Metal Amplification Method", Journal of Applied Physics, (Jun. 1, 2002), pp. 9341-9345, vol. 91, No. 11, 2002 American Institute of Physics.

Ding et al., "Structure Analysis of Nanowires and Nanobelts by Transmission Electron Microscopy", J. Phys. Chem. B, (2004), pp. 12280-12291, vol. 108, No. 33.

Hong et al., "Ultrathin Single-Crystalline Silver Nanowire Arrays Formed in an Ambient Solution Phase", Science, (Oct. 12, 2001), pp. 348-351, vol. 294.

Hurley, L. H. et al., "G-quadruplexes as Targets for Drug Design", Pharmacol Ther., (Mar. 2000), vol. 83, No. 3, pp. 141-158.

Kostko, A. F. et al., "Salt Effects on the Phase Behavior, Structure, and Rheology of Chromonic Liquid Crystals", J. Phys. Chem., (Oct. 20, 2005), vol. 109, No. 41, pp. 19126-19133.

Kumar et al., "Linear Superclusters of Colloidal Gold Particles by Electrostatic Assembly on DNA Templates", Advanced Materials, (Mar. 2, 2001), pp. 341-344, vol. 13, No. 5, Wiley-VCH Verlag GmbH, D-69469 Weinheim.

Medintz et al., "Self-Assembled Nanoscale Biosensors Based on Quantum Dot FRET Donors", Nature Materials, (Sep. 2003), pp. 630-638, vol. 2, Nature Publishing Group.

Zhang et al., "Polymer Microgels: Reactors for Semiconductor, Metal, and Magnetic Nanoparticles", JACS, (2004), 7908-7914, vol. 126, No. 25, American Chemical Society.

PCT Search Report, PCT/US2006/039727.

Huang et al., "Nanowire Arrays Electrodeposited from Liquid Crystalline Phases", Advanced Materials, (Jan. 4, 2002), pp. 61-64, vol. 14, No. 1, Wiley-VCH Verlag GmbH, D-69469 Weinheim.

* cited by examiner

METHOD FOR MAKING CHROMONIC NANOPARTICLES

FIELD

This invention relates to methods for making nanoparticles using chromonic materials, the chromonic nanoparticles optionally containing metals or bioactive compounds.

BACKGROUND

In recent years, there has been increasing research effort to develop metal structures in the nanoscale range (that is, in the 0.1 to 100 nm range) for a variety of technological applications such as, for example, electronic and optical devices, labeling of biological material, magnetic recording media, and quantum computing.

Metallic nanoparticles, having a diameter of about 1-100 nanometers (nm), are important materials for applications that include semiconductor technology, magnetic storage, electronics fabrication, and catalysis. Metallic nanoparticles have been produced by gas evaporation; by evaporation in a flowing gas stream; by mechanical attrition; by sputtering; by electron beam evaporation; by thermal evaporation; by electron beam induced atomization of binary metal azides; by expansion of metal vapor in a supersonic free jet; by inverse micelle techniques; by laser ablation; by laser-induced breakdown of organometallic compounds; by pyrolysis of organometallic compounds; by microwave plasma decomposition of organometallic compounds, and by other methods.

It is known that metallic nanoparticles possess unique optical properties. In particular, metallic nanoparticles display a pronounced optical resonance. This so-called plasmon resonance is due to the collective coupling of the conduction electrons in the metal sphere to the incident electromagnetic field. This resonance can be dominated by absorption or scattering depending on the radius of the nanoparticle with respect to the wavelength of the incident electromagnetic radiation. Associated with this plasmon resonance is a strong local field enhancement in the interior of the metal nanoparticle. A variety of potentially useful devices can be fabricated to take advantage of these specific optical properties. For example, optical filters or chemical sensors based on surface enhanced Raman scattering (SERS) have been fabricated.

U.S. Pat. No. 6,344,272 (Oldenburg et al.) describes nanoparticles comprised of a nonconducting inner layer that is surrounded by an electrically conducting material. The ratio of the thickness of the nonconducting layer to the thickness of the outer conducting shell is determinative of the wavelength of maximum absorbance or scattering of the particle. The reference notes that a serious practical limitation to realizing many applications of solid metal nanoparticles is the inability to position the plasmon resonance at desired wavelengths. For example, solid gold nanoparticles of 10 nm in diameter have a plasmon resonance centered at 520 nm. This plasmon resonance cannot be controllably shifted by more than approximately 30 nanometers by varying the particle diameter or the specific embedding medium.

Surface Plasmon Resonance (SPR) is the resonant excitation of oscillating free charges at the interface of a metal and a dielectric. When SPR spectra are generated and collected, they can be used to determine specificity, kinetics, affinity, and concentration with respect to the interactions between two or more molecules, where one of the molecules is attached to a solid sensing surface. Reaction kinetics corresponds to both an association and a dissociation rate at which an analyte interacts with the bound detection molecule. Affinity refers to the strength with which an analyte binds to the detecting molecule. Specificity refers to the propensity of a molecule to bind to the detecting molecule to the exclusion of other molecules. SPR spectra have been used in studies involving many types of molecules including proteins, peptides, nucleic acids, carbohydrates, lipids, and low molecular weight substances (e.g., hormones and pharmaceuticals).

SPR based bio-sensing, has been developed to enable direct measurements of the association of ligands with receptors, without the use of indirect labels, such as fluorescent markers and radioactive molecular tags. This label free direct sensing technique reduces the time and workload required to perform assays, and minimizes the risk of producing misleading results caused by molecular changes induced by the use of indirect labels. Another important aspect of the bio-sensing technique is that SPR based bio-sensing enables bio-molecular interactions to be measured continuously and in real-time, thereby enabling the determination of association and dissociation kinetic data in contrast to traditional "end point" analytical methods.

Recently, sensor devices have been developed in the known art to exploit the unique optical properties of these nanoparticles. SPR measurements have been made using gold nanoparticle suspensions to detect biomolecular interactions in real time by monitoring the absorbance of colloidal suspensions.

Over the past decade, interest in the unique optical properties of metallic nanoparticles has increased considerably with respect to the use of suspensions and films incorporating these nanoparticles for the purposes of exciting surface plasmons to enable the detection of SPR spectra. In addition, Surface Enhanced Raman Spectroscopy (SERS) for infrared absorbance spectral information and surface enhanced fluorescence for enhanced fluorescence stimulation can also be detected. Nanoparticles are particles that are less than 100 nanometers in diameter. Metallic nanoparticles display large absorbance bands in the visible wavelength spectrum yielding colorful colloidal suspensions. The physical origin of the light absorbance is due to incident light energy coupling to a coherent oscillation of the conduction band electrons on the metallic nanoparticle. This coupling of incident light is unique to discrete nanoparticles and films formed of nanoparticles (referred to as metallic island films). Achieving SPR with ordinary bulk materials requires the use of a prism, grating, or optical fiber to increase the horizontal component of the incident light wave vector (i.e., to achieve the required coupling).

The delivery of a bioactive compound to a living organism is generally affected by a number of parameters beyond the actual chemical identity and pharmacological activity of the bioactive compound. Formulation additives other than the bioactive compound are commonly used to alter the physicochemical properties of a product having bioactive function. As an example, pharmaceutical dosage forms (i.e., dosages containing a drug or active pharmaceutical ingredient) typically contain one or more non-pharmaceutically active ingredients that are referred to as excipients. There are a wide variety of purposes for excipients, just a few examples of which are adjusting the physical form of a dosage (e.g., tablet formation, viscosity adjustment in semi-solids), aiding in drug solubilization or stabilization, or enhancing the uptake of drug in a living organism (e.g., permeation enhancement, selective site targeting).

SUMMARY

In view of the foregoing, it has been recognized that there is a need for a method for making chromonic nanoparticles that provides control over the size and shape of the nanoparticles. As used herein, "nanoparticles" refers to particles of less than 1000 nanometers.

Briefly, in one aspect, the present invention provides a method of making a chromonic nanoparticle dispersion comprising providing an aqueous mixture comprising (i) a continuous water-soluble polymer phase and (ii) a discontinuous chromonic phase comprising a chromonic material; and non-covalently crosslinking the resulting chromonic nanoparticles with a polyvalent cation salt. Optionally the method further comprises contacting the chromonic nanoparticles with a surface-modifying agent. The methods of the invention enable the preparation of metallic nanoparticles with relatively uniform size and shape. Thus, the methods of the invention meet the need in the art for an improved method for making metallic nanoparticles.

In another aspect the invention provides a chromonic nanoparticle dispersion comprising a (i) a continuous water-soluble polymer phase and (ii) a discontinuous chromonic phase comprising a non-covalently crosslinked chromonic material. The chromonic nanoparticles may further comprise a noble metal salt, elemental noble metal, or bioactive compound contained or intercalated within the chromonic nanoparticle matrix. The presence of the water soluble polymer in the continuous phase enables greater control over the size and shape of the resulting chromonic nanoparticles.

As used herein, "chromonic materials" (or "chromonic compounds") refers to large, multi-ring molecules typically characterized by the presence of a hydrophobic core surrounded by various hydrophilic groups (see, for example, Attwood, T. K., and Lydon, J. E., Molec. Crystals Liq. Crystals, 108, 349 (1984)). The hydrophobic core can contain aromatic and/or non-aromatic rings. When in solution, these chromonic materials tend to aggregate into a nematic ordering characterized by a long-range order.

As used herein, "dispersion" means solid chromonic nanoparticles distributed or suspended within a liquid continuous phase that does not separate over a useful time period, for example, minutes, hours, or days.

The present invention also provides a method of making noble metal nanoparticle coatings comprising (a) applying an aqueous composition comprising a non-covalently crosslinked chromonic material containing a noble metal salt to the surface of a substrate; and (b) reducing the noble metal salt to produce a coated substrate having a continuous coating of water soluble polymer and chromonic elemental metal nanoparticles dispersed therein.

In another aspect, the present invention provides articles comprising a chromonic matrix and metal nanoparticles. As used herein, "chromonic matrix" refers to chromonic materials that are aggregated into a nematic ordering.

DETAILED DESCRIPTION

Figure 1:
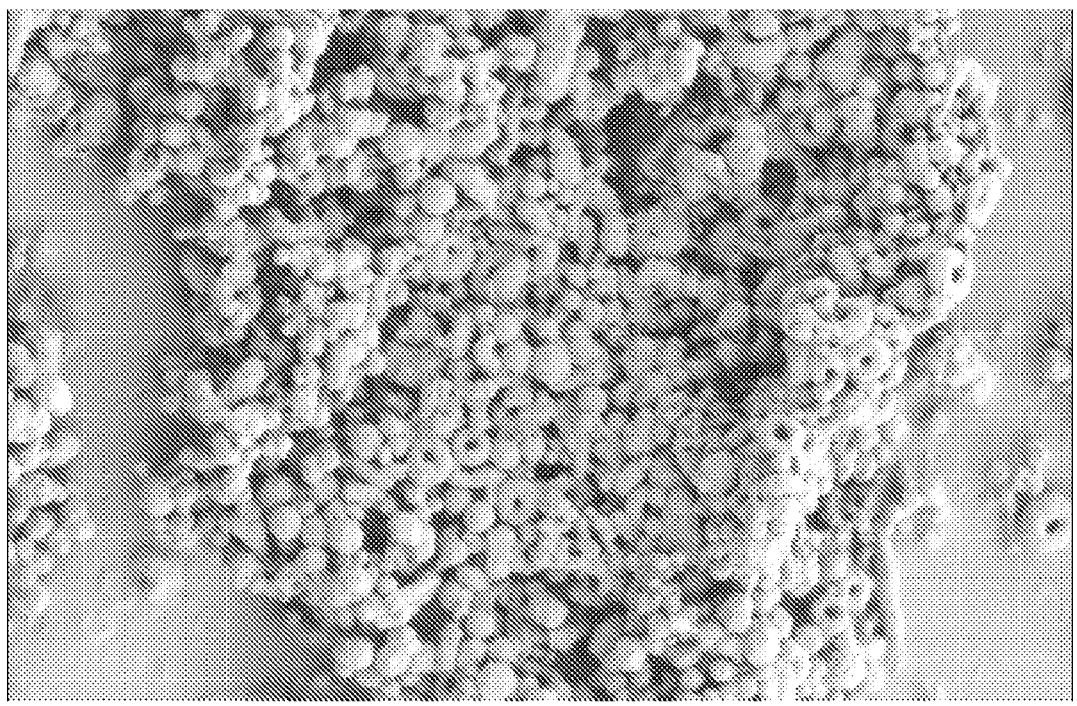
FIG. 1 is digital image of the nanoparticles of Example 1.
Figure 2:
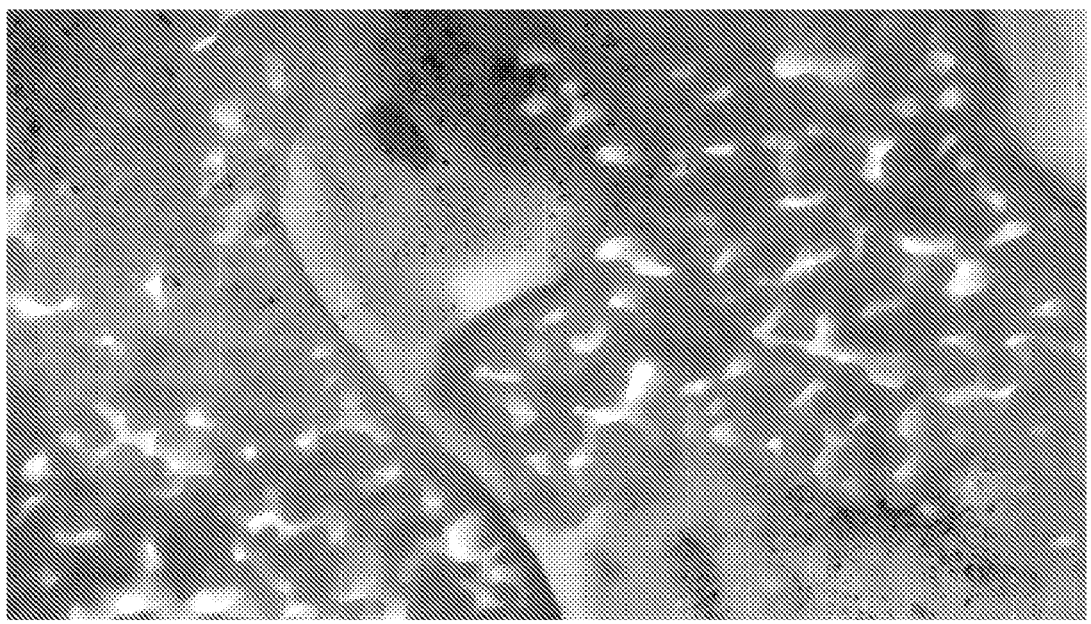
FIG. 2 is a digital image of the nanoparticles of Example 6.

Any chromonic material can be useful in the methods of the invention. Compounds that form chromonic phases are known in the art, and include, for example, xanthoses (for example, azo dyes and cyanine dyes) and perylenes (see, for example, Kawasaki et al., Langmuir 16, 5409 (2000), or Lydon, J., Colloid and Interface Science, 8, 480 (2004). Representative examples of useful chromonic materials include di- and mono-palladium organyls, sulfamoyl-substituted copper phthalocyanines, and hexaaryltryphenylene.

Preferred chromonic materials include those represented by one of the following general structures:

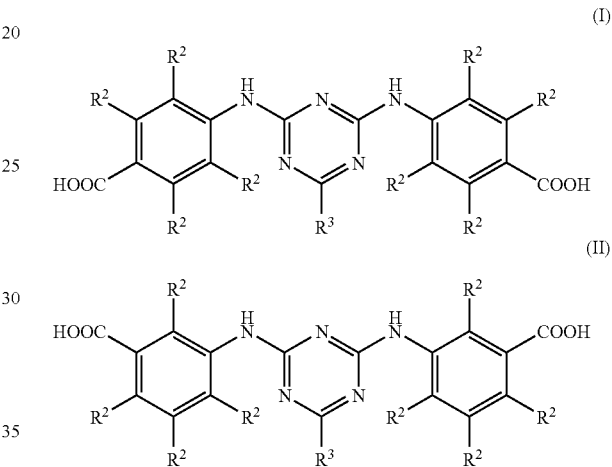

wherein
each $R^2$ is independently selected from the group consisting of electron donating groups, electron withdrawing groups, and electron neutral groups, and $R^3$ is selected from the group consisting of a substituted and unsubstituted heteroaromatic ring, and a substituted and unsubstituted heterocyclic ring, the ring being linked to the triazine group through a nitrogen atom within the ring of $R^3$.

As depicted above, the chromonic compound is neutral, but it can exist in alternative forms such as a zwitterion or proton tautomer (for example, where a hydrogen atom is dissociated from one of the carboxyl groups and is associated with one of the nitrogen atoms in the triazine ring). The chromonic compound can also be a salt such as, for example, a carboxylate salt.

The general structures above show orientations in which the carboxyl group is para with respect to the amino linkage to the triazine backbone of the compound (formula I) and in which the carboxyl group is meta with respect to the amino linkage to the triazine backbone (formula II). The carboxyl group can also be a combination of para and meta orientations (not shown). Preferably, the orientation is para.

Preferably, each $R^2$ is hydrogen or a substituted or unsubstituted alkyl group. More preferably, $R^2$ is independently selected from the group consisting of hydrogen, unsubstituted alkyl groups, alkyl groups substituted with a hydroxy or halide functional group, and alkyl groups comprising an ether, ester, or sulfonyl. Most preferably, $R^2$ is hydrogen.

R³ can be, but is not limited to, a heteroaromatic ring derived from pyridine, pyridazine, pyrimidine, pyrazine, imidazole, oxazole, isoxazole thiazole, oxadiazole, thiadiazole, pyrazole, triazole, triazine, quinoline, and isoquinoline. Preferably, R³ comprises a heteroaromatic ring derived from pyridine or imidazole. A substituent for the heteroaromatic ring R³ can be selected from, but is not limited to, the group consisting of substituted and unsubstituted alkyl, carboxy, amino, alkoxy, thio, cyano, amide, sulfonyl, hydroxy, halide, perfluoroalkyl, aryl, ether, and ester groups. Preferably, the substituent for R³ is selected from the group consisting of alkyl, sulfonyl, carboxy, halide, perfluoroalkyl, aryl, ether, and alkyl substituted with hydroxy, sulfonyl, carboxy, halide, perfluoroalkyl, aryl, or ether. When R³ is a substituted pyridine, the substituent is preferably located at the 4-position. When R³ is a substituted imidazole, the substituent is preferably located at the 3-position.

Representative examples of R³ include 4-(dimethylamino)pyridinium-1-yl, 3-methylimidazolium-1-yl, 4-(pyrrolidin-1-yl)pyridinium-1-yl, 4-isopropylpyridinium-1-yl, 4-[(2-hydroxyethyl)methylamino]pyridinium-1-yl, 4-(3-hydroxypropyl)pyridinium-1-yl, 4-methylpyridinium-1-yl, quinolinium-1-yl, 4-tert-butylpyridinium-1-yl, and 4-(2-sulfoethyl)pyridinium-1-yl, shown below.

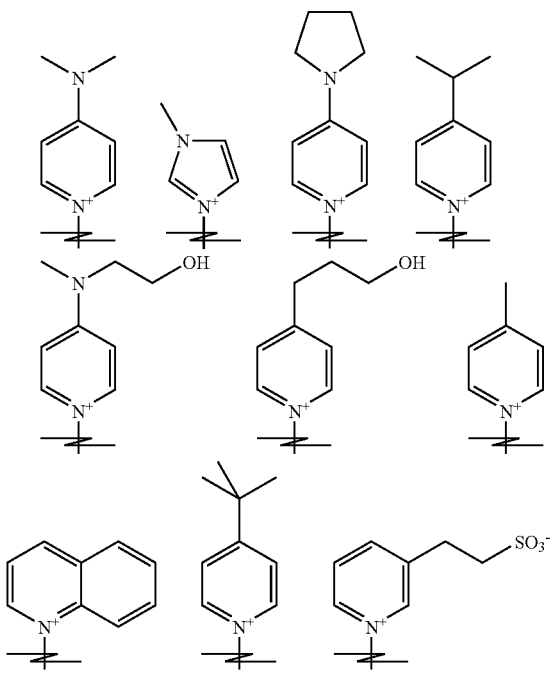

R³ can also be represented by the following general structure:

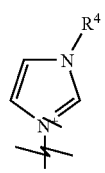

wherein R⁴ is hydrogen or a substituted or unsubstituted alkyl group. More preferably, R⁴ is selected from the group consisting of hydrogen, unsubstituted alkyl groups, and alkyl groups substituted with a hydroxy, ether, ester, sulfonate, or halide functional group. Most preferably R⁴ is selected from the group consisting of propyl sulfonic acid, methyl, and oleyl.

R³ can also be selected from heterocyclic rings such as, for example, morpholine, pyrrolidine, piperidine, and piperazine.

A preferred chromonic compound for use in the methods of the invention can be represented by one of the following structures:

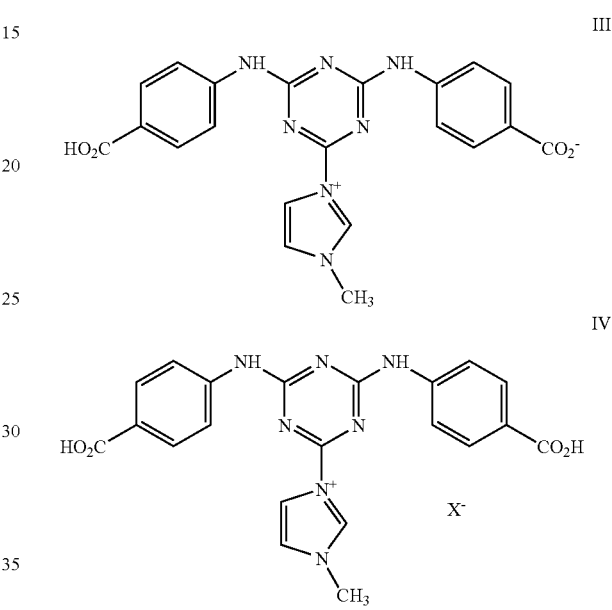

wherein X⁻ is a counterion. Preferably, X⁻ is selected from the group consisting of $HSO_4^-$, $Cl^-$, $CH_3COO^-$, and $CF_3COO^-$.

Formula III depicts the compound in its zwitterionic form. The imidazole nitrogen therefore carries a positive charge and one of the carboxy functional groups carries a negative charge (COO⁻).

The compound can also exist in other tautomeric forms such as where both carboxy functional groups carry a negative charge and where positive charges are carried by one of the nitrogens in the triazine groups and the nitrogen on the imidazole group.

As described in U.S. Pat. No. 5,948,487 (Sahouani et al.), which is herein incorporated by reference in its entirety, triazine derivatives with formula I can be prepared as aqueous solutions. A typical synthetic route for the triazine molecules shown in formula I above involves a two-step process. Cyanuric chloride is treated with 4-aminobenzoic acid to give 4-{[4-(4-carboxyanilino)-6-chloro-1,3,5-triazin-2-yl]amino}benzoic acid. This intermediate is treated with a substituted or unsubstituted nitrogen-containing heterocycle. The nitrogen atom of the heterocycle displaces the chlorine atom on the triazine to form the corresponding chloride salt. The zwitterionic derivative, such as that shown in formula III above, is prepared by dissolving the chloride salt in ammonium hydroxide and passing it down an anion exchange column to replace the chloride with hydroxide, followed by solvent removal. Alternative structures, such as that shown in formula II above, may be obtained by using 3-aminobenzoic acid instead of 4-aminobenzoic acid.

Chromonic materials are capable of forming a chromonic phase or assembly when dissolved in an aqueous solution (preferably, an alkaline aqueous solution). Chromonic phases or assemblies are well known in the art (see, for example, Handbook of Liquid Crystals, Volume 2B, Chapter XVIII, Chromonics, John Lydon, pp. 981-1007, 1998) and consist of stacks of flat, multi-ring aromatic molecules. The molecules consist of a hydrophobic core surrounded by hydrophilic groups. The stacking can take on a number of morphologies, but is typically characterized by a tendency to form columns created by a stack of layers. Ordered stacks of molecules are formed that grow with increasing concentration.

Preferably, the chromonic material is placed in aqueous solution in the presence of one or more pH-adjusting compounds and optionally a surfactant. The addition of pH-adjusting compounds allows the chromonic material to become more soluble in aqueous solution. Suitable pH-adjusting compounds include any known base such as, for example, ammonium hydroxide or various amines. Surfactant can be added to the aqueous solution to promote incorporation of a drug into the matrix of the chromonic naoparticle. Suitable surfactants include ionic and non-ionic surfactants (preferably, non-ionic). Optional additives such as viscosity modifiers (for example, polyethylene glycol) and/or binders (for example, low molecular weight hydrolyzed starches) can also be added.

Typically,-the chromonic materials are dissolved in the aqueous solution at a temperature less than about 40° C. (more typically, at room temperature), and neutralized to pH 6-8 by the addition of a base. The neutralized chromonic material may then be combined with a solution of water-soluble polymer. One skilled in the art will recognize, however, that the geometry and size of the resulting metallic nanoparticles can be controlled to some extent by varying the temperature.

Further, it has been discovered that the particular water-soluble polymer may influence the shape of the metallic nanoparticles. In most instances, spherical metallic nanoparticles are obtained. In another embodiment, acicular (needle-like) metallic nanoparticles have resulted from the use of modified starch. The aspect ratios of the metallic nanoparticles range from 1:4 to 1:10, and have lengths from 300 nanometers to about 5 millimeters. In yet another embodiment, oblate spheroidal or toroidal shapes may be obtained.

The aqueous composition comprising a chromonic material can be mixed with a non-chromonic phase comprising a water-soluble polymer. Preferably, the water-soluble polymer has a molecular weight of less than about 20,000.

Useful water-soluble polymers include, for example, polyvinyl-based water-soluble polymers, polycarboxylates, polyacrylates, polyamides, polyamines, polyglycols, cellulosics, starches and modified starches, and the like, and mixtures thereof. Copolymers, for example, block or random copolymers can also be useful. Preferred water-soluble polymers include, for example, cellulosics, starches (including modified starches such as phosphonated or sulfonated starches) polyvinyl alcohol, polyethylene glycol, polypropylene glycol, poly(ethylene glycol)-co-(propylene glycol), and mixtures thereof.

The relative concentrations of each of the components in the aqueous solution will vary with the desired size of the resulting nanoparticles and their intended application. Generally, however, the chromonic material will be added to the solution of water-soluble polymer in amounts sufficient such that the chromonic phase is discontinuous and the water-soluble polymer phase is continuous. The amounts of water-soluble polymer and chromonic material are generally selected so that the ratio is at least about 5:1 and less that about 99:1, and preferably 3:1 to 15:1 on a dry weight basis. Generally, the water-soluble polymer comprises 15 to 25 wt. % of the aqueous mixture. Generally, the concentration of chromonic material is from 0.25 to 7 wt. % of the aqueous mixture.

Optionally, surfactants and other additives (for example, short chain alcohols such as ethanol) that increase surface tension or promote coating can be added.

The water-insoluble discontinuous phase of the present invention is comprised of chromonic materials that are non-covalently crosslinked by multivalent cations. This crosslinking forms a three-dimensional matrix that is insoluble in water. By non-covalent, it is meant that the crosslinking does not involve permanently formed covalent (or chemical) bonds. That is, the crosslinking does not result from a chemical reaction that leads to a new, larger molecule, but rather results from associations of the cations with the host molecules that are strong enough to hold them together without undergoing a chemical reaction. These interactions are typically ionic in nature and can result from interaction of a formal negative charge on the host molecule with the formal positive charge of a multivalent cation. Since the multivalent cation has at least two positive charges, it is able to form an ionic bond with two or more chromonic molecules, that is, a crosslink between two or more chromonic molecules. Divalent and/or trivalent cations are preferred. It is more preferred that a majority of the multivalent cations are divalent. Suitable cations include any divalent or trivalent cations, with calcium, magnesium, zinc, aluminum, and iron being particularly preferred.

Generally, the chromic material is crosslinked after formation of the dispersion comprising a continuous phase of water-soluble polymer and discontinuous phase of chromonic material. Typically, the dispersion is added to a solution of excess polyvalent cation salt.

Subsequent to non-covalent crosslinking, the nanoparticles may be contacted with a surface-modifying agent to render the particles more hydrophilic, hydrophobic, biocompatible, or bioactive. The surface groups are present on the surface of the particle in an amount sufficient to provide surface-modified chromonic nanoparticles that are capable of being subsequently dispersed in the continuous phase without aggregation. The surface groups preferably are present in an amount sufficient to form a monolayer, preferably a continuous monolayer, on the surface of the chromonic nanoparticle. Generally, the crosslinked chromonic nanoparticle is first isolated from the water-soluble polymer dispersion, then resuspended in a solution of surface modifying agent.

Surface modifying groups may be derived from surface modifying agents. Schematically, surface modifying agents can be represented by the formula A-B, where the A group is capable of attaching to the surface of the chromonic nanoparticle and the B group is a compatibilizing group that confers the desired hydrophilicity, hydrophobicity or biocompatibility. Compatibilizing groups can be selected to render the particle relatively more polar, relatively less polar or relatively non-polar.

Suitable classes of surface-modifying agents include organic oxyacids of carbon, sulfur and phosphorus, for example, alkylcarboxylates, alkyl sulfates, alkylsulfonates, alkyl phosphates and alkylphosphonates, glycoside phosphonates and combinations thereof.

Representative examples of polar surface-modifying agents having carboxylic acid functionality include poly(ethylene glycol) monocarboxylic acid having the chemical structure $CH_3O(CH_2CH_2O)_nCH_2COOH$ (n=2-50) and 2-(2-methoxyethoxy)acetic acid having the chemical structure $CH_3OCH_2CH_2OCH_2COOH$ in either acid or salt forms.

Representative examples of non-polar surface-modifying agents having carboxylic acid functionality include octanoic acid, dodecanoic acid and oleic acid in either acid or salt form. In the case of a carboxylic acid containing olefinic unsaturation, such as oleic acid, the carbon-carbon double bonds may be present as either the Z or E stereoisomers or as a mixture thereof.

Examples of suitable phosphorus containing acids include alkylphosphonic acids including, e.g., octylphosphonic acid, decylphosphonic acid, dodecylphosphonic acid, octadecylphosphonic acid, oleylphosphonic acid and poly(ethylene glycol) monophosphonic acid having the chemical structure $CH_3O(CH_2CH_2O)_nCH_2CH_2PO_3H_2$ (n=2-50) in either acid or salt forms. In the case of a phosphonic acid containing olefinic unsaturation, such as oleylphosphonic acid, the carbon-carbon double bonds may be present as either the Z or E stereoisomers or as a mixture thereof.

Additional examples of suitable phosphorus containing acids include alkyl phosphates such as mono- and diesters of phosphoric acid including, e.g., octyl phosphate, dodecyl phosphate, oleyl phosphate, dioleyl phosphate, oleyl methyl phosphate and poly(ethylene glycol) monophosphoric acid having the chemical structure $CH_3O(CH_2CH_2O)_nCH_2CH_2OPO_3H_2$ (n=2-50).

In some modifications, the B group of the surface modifying agent A-B can also contain an additional specific functional group(s) to further adjust the hydrophilicity, hydrophobicity or biocompatibility of the chromonic nanoparticle. Suitable functional groups include, but are not limited to the hydroxyl, carbonyl, ester, amide, ether, amino, and quaternary ammonium functions.

If biocompatibility is desired, the chromonic nanoparticles may be surface modified with glycosides phosphonates, e.g. glucosides, mannosides, and galactosides of phosphonic acid.

The aqueous composition comprising a chromonic material and water-soluble polymer can be mixed with a noble metal salt in solution to produce metallic chromonic nanoparticles. Subsequently the mixture may to contacted with a polyvalent cation salt to non-covalently crosslink the chromonic material and incorporate the noble metal salt.

Preferred metal salts include silver salts (for example, silver nitrate, silver acetate, and the like), gold salts (for example, gold sodium thiomalate, gold chloride, and the like), platinum salts (for example, platinum nitrate, platinum chloride, and the like), and mixtures thereof. Most preferred metal salts include, silver nitrate, silver acetate, gold sodium thiomalate, gold chloride, and mixtures thereof. Other transition metal salts may also be used. In particular, salts of monovalent transition metal cations may be used.

The resulting mixture can be applied to the surface of a substrate. Suitable substrates include any solid materials that will accept the application of the mixture (for example, glass or polymeric films).

The metal salt can be reduced via reduction methods known in the art either before or after applying the mixture to the surface of a substrate. For example, the reduction can be accomplished by using a reducing agent (for example, tris (dimethylamino)borane, sodium borohydride, potassium borohydride, or ammonium borohydride), electron beam (e-beam) processing, or ultraviolet (UV) light.

After the metal salt is reduced, the coated layer can be dried and the chromonic material can be removed such that only metallic nanoparticles remain on the substrate as described above. The methods can be used to make spherical metallic nanoparticles that are substantially evenly spaced on a substrate surface.

The mixture can be applied by any useful means that provides for the ordered arrangement of the chromonic materials such as, for example, by coating techniques such as wire-wound coating rod or extrusion die methods-to produce a coated substrate having a metallic nanoparticle coating thereof, the crosslinked chromonic nanoparticles having a noble metal salt intercalated therein. Optionally, shear orientation or magnetic orientation is applied to the mixture either during or after application. The application of shear or magnetic force to the mixture can help promote alignment of the chromonic materials such that, upon drying, an oriented structure or matrix is obtained.

Drying of the coated layer can be achieved using any means suitable for drying aqueous coatings. Useful drying methods will not damage the coating or significantly disrupt the orientation of the coated layer imparted during coating or application.

After drying, the chromonic material can be removed such that only metallic nanoparticles remain on the substrate. The chromonic material can be removed using any means such as, for example by heating to decomposition (for example, by heating to higher than about 300° C.). Alternatively, if the substrate is glass, the chromonic material can be removed with a basic solution.

After drying, the water-soluble polymer can be removed such that only the chromonic matrix (containing metallic or metal nanoparticles) remains on the substrate as discreet nanoparticles. For example, the higher the concentration of water-soluble polymer, the greater the spacing between chromonic nanoparticles.

Advantageously, unlike in other systems that phase separate (for example, polymer-polymer systems), the water-soluble polymer can be easily removed from the chromonic material. For example, the water-soluble polymer can be removed by heating to a temperature higher than the temperature at which the water-soluble polymer decomposes, but lower than which the chromonic material decomposes (for example, by heating to between about 200° C. and 350° C.). Alternatively, the chromonic material can be rendered insoluble (for example, by protonization or amidization (that is, by reaction with diamine), or by thermally decomposing ammonium salts by heating to about 250° C.), and the water-soluble polymer can be removed with water.

The metallic chromonic nanoparticles may be used in such diverse applications as medical imaging, optical switching devices, optical communication systems, infrared detectors, infrared cloaking devices, chemical sensors, passive solar radiation collection or deflecting devices and the like.

In another embodiment, the present invention provides a composition for encapsulation and controlled release comprising a water-insoluble matrix comprising a chromonic host molecule that is non-covalently crosslinked by multivalent cations. The composition is characterized in that a bioactive compound may be encapsulated within the matrix and subsequently released.

The composition is characterized in that a guest molecule may be encapsulated and released. Examples of useful guest molecules include dyes, cosmetic agents, fragrances, flavoring agents, and bioactive compounds, such as drugs, herbicides, pesticides, pheromones, and antifungal agents. A bioactive compound is herein defined as a compound intended for use in the diagnosis, cure, mitigation, treatment or prevention of disease, or to affect the structure or function of a living organism. Drugs (i.e., pharmaceutically active ingredients) are particularly useful guest molecules, which are intended to have a therapeutic effect on an organism. Alternatively, herbicides and pesticides are examples of bioactive compounds intended to have a negative effect on a living organism, such as a plant or pest. Although any type of drug may be employed with compositions of the present invention, particularly suitable drugs include those that are relatively unstable when formulated as solid dosage forms, those that are adversely affected by the low pH conditions of the stomach, those that are adversely affected by exposure to enzymes in the gastrointestinal tract, and those that are desirable to provide to a patient via sustained or controlled release.

The guest-host complex will selectively protect a drug from certain environmental conditions and then controllably deliver the drug under other environmental conditions. In one aspect, the matrix will be stable in the acidic environment of the stomach and will dissolve when passed into the non-acidic environment of the intestine when administered to an animal, i.e. as result of a change in pH. In another aspect, the matrix will protect a drug from enzymatic degradation.

The present invention can also provide a matrix that will effectively isolate drug molecules in a particle, such that unfavorable interactions (e.g., chemical reactions) between different drugs in a combination dosage form, unfavorable changes in a single drug component (e.g., Ostwald ripening or particle growth, changes in crystalline form), and/or unfavorable interactions between a drug and one or more excipients can be avoided. In one aspect, the matrix of the present invention would allow two drugs that are ordinarily-unstable in each other's presence to be formulated-into a stable dosage form. In another aspect, the matrix of the present invention would allow a drug and excipient that are ordinarily unstable in each other's presence to be formulated into a stable dosage form.

The present invention can also provide a method of preparing a matrix that will selectively protect a drug from certain environmental conditions by a process of directly mixing a chromonic host molecule, a guest bioactive molecule, and a multivalent crosslinking ion.

Nanoparticles may be prepared by mixing the chromonic host molecules with multivalent cations. Typically this is done by dissolving the chromonic host molecule in an aqueous solution and subsequently adding multivalent cations to cause precipitation of the nanoparticles, or alternatively, by adding an aqueous solution of dissolved chromonic host molecules to a solution of multivalent cations. Drugs (or other guest molecules) may be contained or intercalated in the matrix by adding drug to either the aqueous solution of host molecules or the multivalent cation solution prior to precipitation. Alternatively, a drug may be dispersed or dissolved in another excipient or vehicle, such as an oil or propellant, prior to mixing with the host molecules or multivalent cation solutions. Particles may be collected by, for example, filtration, spraying, or other means and dried to remove the aqueous carrier.

In one aspect, a guest molecule, such as a drug, may be dissolved in an aqueous dispersant-containing solution prior to introduction of the chromonic host molecule, the solution. Suitable dispersant include alkyl phosphates, phosphonates, sulfonates, sulfates, or carboxylates, including long chain saturated fatty acids or alcohols and mono or poly-unsaturated fatty acids or alcohols. Oleyl phosphonic acid is an example of a suitable dispersant. Although not to be bound by any particular theory, it is thought that the dispersant aids in dispersing the guest molecule so that it may be better encapsulated.

An alkaline compound may be added to the guest molecule solution prior to introduction of the chromonic host molecule. Alternatively, an alkaline compound may be added to a chromonic host molecule solution prior to mixing the guest molecule and chromonic host molecule solutions. Examples of suitable alkaline compounds include ethanolamine, sodium or lithium hydroxide, or amines such as mono, di, triamines or polyamines. Although not to be bound by theory, it is thought that alkaline compounds aid in dissolving the host compound, particularly where the host compound is a triazine compound such as those described in formulas I and II above.

Although large particles (e.g., on the order of several millimeters in diameter) may be prepared, the mass median diameter of particles of the present invention is typically less than 1000 nanometers in size, usually less than 500 nanometers in size, and in some cases less than 100 nanometers in size. In certain instances it may be desired to have particles greater than 1 µm in size. In particular, these particle sizes may be desirable for oral delivery of drugs that are unstable in the intestine due to the presence of certain enzymes. Examples of such drugs include proteins, peptides, antibodies, and other biologic molecules that may be particularly sensitive to the body's enzymatic processes. In such cases, these small particles may be taken up into the intestinal wall directly, such that the particle primarily dissolves after passing the intestinal barrier, so that the amount of the sensitive drug exposed to the intestinal environment is minimized. Particles are typically spherical in their general shape, but may also take any other suitable shape, such as needles, cylinders, or plates.

The particles are dissolvable in an aqueous solution of univalent cations or other non-ionic compounds, such as surfactants. Typical univalent cations include sodium and potassium. The concentration of univalent cations needed to dissolve the particles will depend on the type and amount of the host molecules within the matrix, but for complete dissolution of the particles there should generally be at least a molar amount of univalent cations equivalent to the molar amount of carboxyl groups in the matrix. In this way, there will be at least one univalent cation to associate with each carboxyl group.

The rate at which a particle dissolves may also be adjusted by adjusting the type and amount of multivalent cation used for crosslinking. Although divalent cations will be sufficient to crosslink the matrix, higher valency cations will provide additional crosslinking and lead to slower dissolution rates. In addition to valency, dissolution rate will also depend on the particular cation type. For example, a non-coordinating divalent cation, such as magnesium, will generally lead to faster dissolution than a coordinating divalent cation, such as calcium or zinc, which has an empty electron orbital capable of forming a coordination bond with a free electron pair.

Different cation types may be mixed so as to give an average cation valency that is not an integer. In particular, a mixture of divalent and trivalent cations will generally cause a slower dissolution rate than a like matrix where all of the cations are divalent. In one aspect, all of the guest molecules will be released over time, but it may be desired in certain applications to have only a portion of the guest molecules be released. For instance, the type or amount of host molecule and multivalent cation may be adjusted such that the total amount of guest molecules that are released will vary depending on the environment into which they are placed. In one embodiment, the particles will not dissolve in an acidic solution, thus protecting acid sensitive guest molecules from degradation. In another, the particles will not dissolve in an acidic solution containing univalent cations, thus protecting acid sensitive guest molecules from degradation.

In the particular instance where the guest molecule is a drug, two common types of general release profiles that are desired are immediate or sustained. For immediate release use it is typically desired that most of the drug will be released in a time period of less than about 4 hours, generally less than about 1 hour, often less than about 30 minutes, and in some cases less than about 10 minutes. In some instances it will desired that drug release will be nearly instantaneous, that is it will take place in a matter of seconds. For sustained (or controlled) release uses it is typically desired that most of the drug will be released over a time period greater than or equal to about 4 hours. Periods of one month or more may be desired, for example in various implantable applications. Oral sustained release dosages will generally release most of the drug over a time period of about 4 hours to about 14 days, sometimes about 12 hours to about 7 days. In one aspect it may be desired to release most of the drug over a time period of about 24 to about 48 hours.

A combination of immediate and sustained release may also be desired, where for instance; a dosage provides an initial burst of release to rapidly alleviate a particular condition followed by a sustained delivery to provide extended treatment of the condition.

In some instances it may be desirable to have a pulsatile or multi-modal release of drug, such that the rate of release varies over time, for instance increasing and decreasing to match the circadian rhythm of an organism. Likewise, it may be desirable to provide a delayed release of drug, such that a dosage may be administered at a convenient time, such as just before going to sleep, but prevent release of the drug until a later time when it may be more efficacious, such as just before waking. One approach for achieving pulsatile, multi-modal, or delayed release profiles may be to mix two or more types of particles having different drug release characteristics. Alternatively, particles may be formed having two or more distinct phases, such as a core and shell, having different drug release characteristics.

Nanoparticles of the present invention that encapsulate a drug find particular use in oral dosage drug delivery. Typical oral dosage forms include solid dosages, such as tablets and capsules, but may also include other dosages administered orally, such as liquid suspensions and syrups. In one aspect, the compositions of the present invention will be particles that are stable in acidic solution and that will dissolve in an aqueous solution of univalent cations. In another aspect, the particles will be stable in the acidic environment of the stomach and will dissolve when passed into the non-acidic environment of the intestine when administered to an animal. When the particles are stable in acidic solution, the particles may generally be stable for periods of time longer than 1 hour, sometimes more than 12 hours, and may be stable for more than 24 hours when present in an acidic environment with a pH less than 7.0, for example less than about 5.0, and in some cases less than about 3.0.

Objects and advantages of this invention are further illustrated by the following examples, but the particular materials and amounts thereof recited in these examples, as well as other conditions and details, should not be construed to unduly limit this invention.

EXAMPLES

Objects and advantages of this invention are further illustrated by the following examples, but the particular materials and amounts thereof recited in these examples, as well as other conditions and details, should not be construed to unduly limit this invention.

Unless otherwise noted, all reagents and solvents were or can be obtained from Sigma-Aldrich Co., St. Louis, Mo.

As used herein, "HPMC" refers to hydroxypropylmethylcellulose having a number average molecular weight of approximately 10,000;

"purified water" refers to water available under the trade designation "OMNISOLVE" from EMD Chemicals, Inc., Gibbstown, N.J.

Preparative Example 1

Preparation of Oleyl Phosphonate

A mixture of 60.0 g (0.209 mol) of oleyl chloride (obtained from TCI America, Portland, Oreg.) and 84.2 g (0.525 mol) of triethyl phosphite (obtained from Alfa Aesar, Ward Hill, Mass.) was stirred and heated at 150° C. After 2 days, an additional 87.0 g (0.524 mol) of triethyl phosphite was added, and heating was continued. After an additional 6 days, an additional 87.0 g (0.524 mol) of triethyl phosphite was added, and the reaction temperature was raised to 170° C. After 14 days more, the mixture was distilled under reduced pressure, and then bulb-to-bulb distillation of the concentrated mixture afforded 78.3 g of oleyl diethyl phosphonate as a clear, colorless liquid (b.p. 170-185° C. at 4 Pa (0.03 mm Hg)). To a solution of 48.6 g (0.125 mol) of oleyl diethyl phosphonate in 150 mL of dichloromethane there was added dropwise with stirring 42.1 g (0.275 mol) of bromotrimethylsilane. After 24 hours at room temperature, the solution was concentrated using a rotary evaporator, and then the resultant mixture was dissolved in 250 mL of methanol. This solution was stirred at room temperature for 1 hour and then the mixture was concentrated using a rotary evaporator. Dissolution in methanol and concentration were repeated two times. The resultant product was dissolved in 500 mL of hexanes, and this solution was filtered. The filtrate was chilled in dry ice and then the precipitated solid was collected by filtration and was washed with cold hexanes, providing 28.6 g of oleyl phosphonic acid as a white solid. The $^1H$, $^{13}C$, and $^{31}P$ NMR spectra of the product were consistent with the assigned structure.

Preparative Example 2

Preparation of Poly(ethylene glycol) Phosphonic Acid

To 750.0 g of poly(ethylene glycol) methyl ether having a number average molecular weight of approximately 2000 (obtained from Clariant Corp., Mount Holly, N.C.) at 60° C. was added 59.5 g of thionyl chloride dropwise with stirring. Evolved gases were vented through a trap containing 25% aqueous sodium hydroxide. After the addition was complete, the temperature of the reaction mixture was raised to 70° C. After 5 h, nitrogen was slowly bubbled through the mixture as the temperature was raised to 90° C., and the reaction mixture was held at 90° C. overnight with continued nitrogen bubbling. Remaining volatiles were separated by heating for 90 min at 125° C. under reduced pressure, and the crude product was used without further purification.

A mixture of this crude product and 187 g of triethyl phosphite was stirred and heated at 150° C. After 3 days, an additional 187 g of triethyl phosphite was added, and the temperature was increased to 160° C. After an additional 2 days at 160° C., a third portion of 187 g of triethyl phosphite was added, and heating at 160° C. was continued for an additional 6 days. Volatiles components were then distilled from the mixture to a final bath temperature of 130° C. at 6.67 Pa (0.05 mm Hg), and the crude product was used without further purification.

To a solution of this product in 1 liter of dichloromethane was added 153.1 g of bromotrimethylsilane. This mixture was stirred at room temperature for 18 hours, and then the solution was concentrated under reduced pressure to a final bath temperature of 110° C. The concentrate was cooled to 50° C., the product was dissolved in 750 mL of methanol, and the resultant solution was stirred at room temperature overnight. The mixture was concentrated under reduced pressure to a final bath temperature of 110° C., the concentrate was again dissolved in 750 mL of methanol, and the resultant solution was stirred overnight at 40° C. The mixture was concentrated again, and the concentrate was maintained overnight at 80° C. under vacuum to remove the volatile components. Cooling to room temperature afforded 757 g of a white waxy solid. The $^1$H, $^{13}$C, and $^{31}$P NMR spectra of the final product and all intermediates were consistent with the assigned structures.

Example 1

Preparation of Chromonic Nanoparticles

An aqueous solution containing 20 weight percent chromonic compound of Formula IV and 0.8 weight percent oleyl phosphonic acid (based on weight of total solution) was prepared using purified water. One part by weight of this solution was combined with 15 parts by weight of a 25 weight percent aqueous solution of HPMC and the mixture was stirred using a mechanical stirrer. One drop of this solution was added to a 10 weight percent aqueous solution of $ZnCl_2$ (3 mL) and the mixture was allowed to stand at room temperature without stirring for 4 hours. After this time, the product mixture, comprising chromonic nanoparticles, was transferred to a poly(ethylene) centrifuge tube. The mixture was centrifuged for 15 minutes and then the supernatant liquid was decanted. Purified water was added to the centrifuge tube and the mixture was again centrifuged for 15 minutes. Decanting the supernatant liquid afforded the product. The product was further analyzed by dynamic light scattering using a Model ZEN3600 particle size analyzer (available from Malvern Instruments, Southborough, Mass.) and was found to have a mean particle size of approximately 662 nanometers.

Example 2

Preparation of Chromonic Nanoparticles

The procedure of Example I was followed; except that 20 weight percent of the 25 weight percent aqueous solution of HPMC was used. The product was analyzed by dynamic light scattering using a Model ZEN3600 particle size analyzer (available from Malvern Instruments, Southborough, Mass.) and was found to have a mean particle size of approximately 569 nanometers.

Example 3

Preparation of Chromonic Nanoparticles

An aqueous solution of the chromonic compound of Formula IV was prepared by stirring together 2.02 g of the chromonic compound, 7.67 g purified water and sequentially adding to this mixture eight drops of 50 weight percent aqueous NaOH, five drops of 25 weight percent aqueous NaOH, and two drops of 5 weight percent aqueous NaOH. The pH of the resultant mixture was approximately 7.5. To a stirred 3.02 g portion of this mixture there was then added 0.087 g of a three weight percent aqueous solution of oleyl phosphonic acid. A 0.32 g portion of the chromonic/oleyl phosphonic acid mixture was added with mechanical stirring to 6.42 g of a 25 weight percent aqueous solution of HPMC. One drop of this mixture was added to 3 milliliters of a 10 weight percent aqueous solution of $ZnCl_2$ and the solution was allowed to stand at room temperature for 30 minutes. After this time, the product mixture, comprising chromonic nanoparticles, was transferred to a poly(ethylene) centrifuge tube. The mixture was centrifuged for 15 minutes and then the supernatant liquid was decanted. Purified water was added to the centrifuge tube and the mixture was again centrifuged for 15 minutes. The supernatant liquid was decanted to afford the product.

Example 4

Preparation of Chromonic Nanoparticles Including Bovine Insulin

An aqueous solution of the chromonic compound of Formula IV was prepared by stirring together 3.34 g of the chromonic compound, 6.59 g purified water, 20 drops of 50 weight percent aqueous NaOH, and 2 drops of 1N aqueous HCl. The pH of the resultant chromonic solution was 7.25. A solution of insulin from bovine pancreas (obtained from Sigma-Aldrich Co., St. Louis, Mo.) was prepared by first stirring together 0.043 g of bovine insulin and 2.6 g of purified water, and then sequentially adding 100 microliters of 1N aqueous HCl, 100 microliters of 3 weight percent aqueous oleyl phosphonic acid, 100 microliters of 5 weight percent aqueous NaOH, and one drop of 1N aqueous HCl to the stirred mixture to afford a mixture having a pH of 7.2. A 1.6 g portion of the insulin mixture was added to a stirring 2.04 g portion of the chromonic mixture. A 0.5 g portion of the insulin/chromonic mixture was then mechanically stirred with 2.51 g of a 25 weight percent aqueous solution of HPMC. Stirring was continued for 15 minutes after which time a 0.63 g portion of the stirred mixture was added to 14.03 g of an aqueous solution that was 1 weight percent $ZnCl_2$ and 9 weight percent $CaCl_2$. This mixture was allowed to stand at room temperature for 15 minutes, after which time it was gently shaken by hand. The product mixture, comprising chromonic nanoparticles, was then transferred to a poly(ethylene) centrifuge tube. The mixture was centrifuged for 15 minutes and then the supernatant liquid was decanted. Purified water was added to the centrifuge tube and the mixture was again centrifuged for 15 minutes. The supernatant liquid was decanted to afford the product.

Example 5

Preparation of Chromonic Nanoparticles

An aqueous solution of the chromonic compound of Formula IV was prepared by stirring together 1.99 g of the chromonic compound, 8.14 g purified water, 9 drops of 50 weight percent aqueous NaOH, and 4 drops of 1N aqueous HCl. The pH of the resultant chromonic solution was 7.4. Separately, an aqueous solution of MPEG phosphonic acid was prepared by stirring together 0.194 g of the PEG phosphonic acid, 1.94 g of purified water, one drop of 25 weight percent aqueous NaOH and one drop of 1N aqueous HCl. The pH of this solution of PEG phosphonic acid was 8.36. A 1.07 g portion of the PEG phosphonic acid solution was stirred with 8.02 g of a 25 weight percent aqueous solution of HPMC. To a stirring 2.07 g portion of this HPMC mixture there was added 0.17 g of the chromonic solution. A 0.55 g portion of this mixture was added to 12.39 g of a 10 weight percent aqueous solution of $ZnCl_2$ and this mixture was allowed to stand for one hour. The product mixture, comprising chromonic nanoparticles, was then transferred to a poly(ethylene) centrifuge tube. The mixture was centrifuged for 15 minutes and then the supernatant liquid was decanted. Purified water was added to the centrifuge tube and the mixture was again centrifuged for 15 minutes. The supernatant liquid was decanted to afford the product. The product was analyzed by scanning electron microscopy. FIG. 1 is a scanning electron micrograph of the chromonic nanoparticles.

Example 6

Preparation of Chromonic Nanoparticles Including Silver Nanoparticles

Silver nitrate (0.44 g) was dissolved in two milliliters of purified water. A 30 weight percent aqueous solution of ammonium hydroxide was then added dropwise to the stirring silver nitrate solution until the solution turned brown in color and then colorless. A 0.2 g portion of this silver nitrate solution was stirred with 0.8 g of a 33 weight percent aqueous solution of the chromonic compound of Formula IV. A 0.5 g portion of this mixture was then mechanically stirred with 6 g of a 25 weight percent aqueous solution of HPMC. The open container of this mixture was left overnight in a sealed chamber with an open container of tris(dimethylamino)borane in order to reduce the silver salt to elemental silver nanoparticles. A 0.6 g portion of this mixture was then added to an excess of 10 weight percent aqueous zinc chloride and this mixture was allowed to stand for 15 minutes and was then gently shaken for approximately one hour. The product mixture, comprising chromonic nanoparticles that included silver nanoparticles, was then transferred to a poly(ethylene) centrifuge tube. The mixture was centrifuged for 20 minutes at 3200 revolutions per minute and then the supernatant liquid was decanted. Purified water was added to the centrifuge tube and the mixture was gently shaken for approximately 30 minutes and was again centrifuged for 15 minutes. The supernatant liquid was decanted to afford the product.

Example 7

Preparation of Chromonic Nanoparticles Using a Cationic Starch

Figure 3:
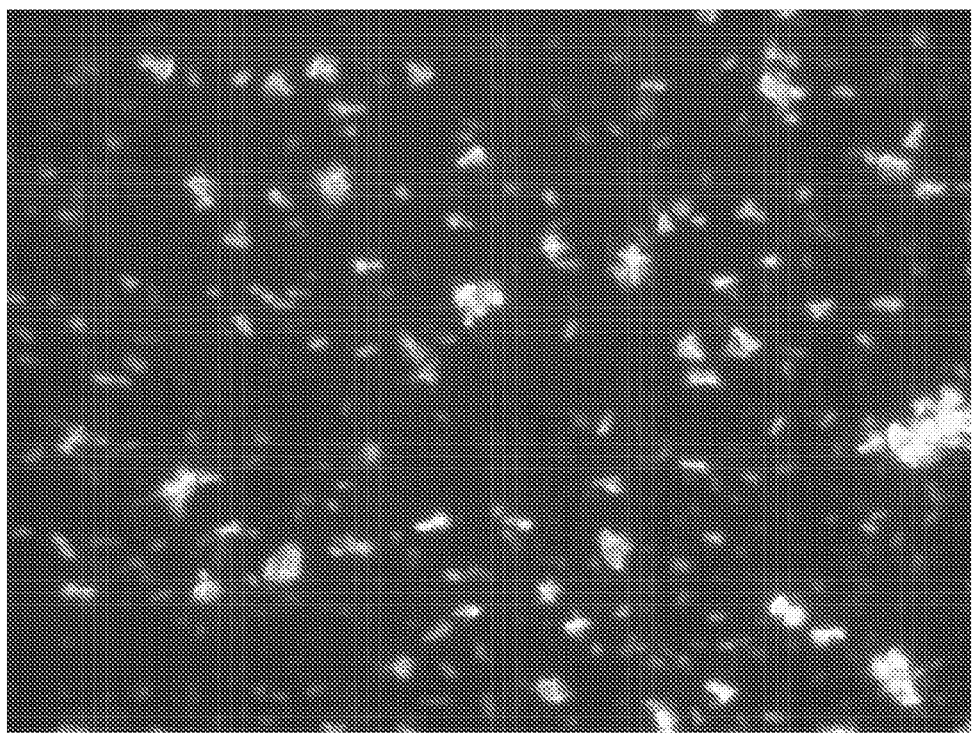
FIG. 3 is a digital image of the nanoparticles of Example 7.

A 20 weight percent aqueous solution of the chromonic compound of Formula III was stirred into a 10 weight percent aqueous solution of STA-LOK 156 (a modified starch available from Tate & Lyle PLC, London, United Kingdom) in a ratio of one part by weight of the chromonic solution to twelve parts by weight of the modified starch solution. After 30 minutes, an aliquot of the mixture was added to an excess of a 10 weight percent aqueous solution of $ZnCl_2$ and the mixture was allowed to stand. The product mixture was then transferred to a poly(ethylene) centrifuge tube. The mixture was centrifuged for 20 minutes at 3200 revolutions per minute and then the supernatant liquid was decanted. Purified water was added to the centrifuge tube and the mixture was gently shaken for approximately 30 minutes and was again centrifuged for 15 minutes. The supernatant liquid was decanted to afford the product. An optical micrograph of the product, taken at 100×, is shown in FIG. 3.

Example 8

Figure 4:
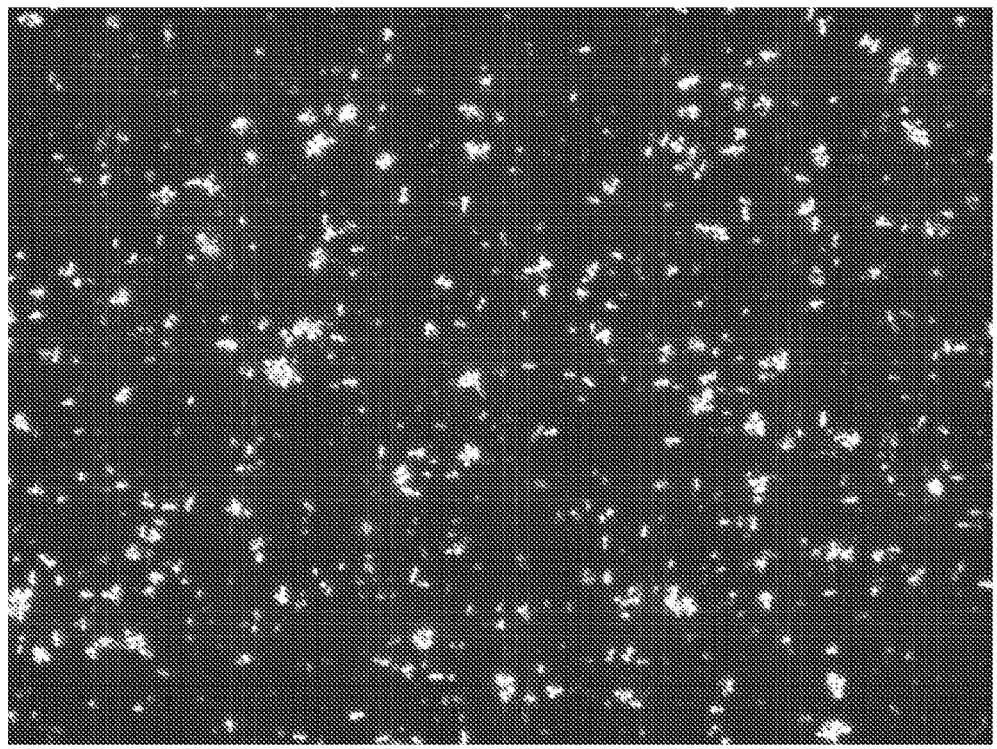
FIG. 4 is a digital image of the nanoparticles of Example 8.

Preparation of Chromonic Nanoparticles Including Fluorescent Bovine Serum Albumin A solution that was 20 weight percent of the chromonic compound of Formula III and 1 weight percent fluorescein isothiocyanate conjugate bovine serum albumin (available from Sigma-Aldrich Co., St. Louis, Mo.) was stirred into a 10 weight percent aqueous solution of STA-LOK 156 (a modified starch available from Tate & Lyle PLC, London, United Kingdom) in a ratio of one part by weight of the chromonic solution to twelve parts by weight of the modified starch solution. After 30 minutes, an aliquot of the mixture was added to an excess of a 10 weight percent aqueous solution of $ZnCl_2$ and the mixture was allowed to stand. The product mixture was then transferred to a poly(ethylene) centrifuge tube. The mixture was centrifuged for 20 minutes at 3200 revolutions per minute and then the supernatant liquid was decanted. Purified water was added to the centrifuge tube and the mixture was gently shaken for approximately 30 minutes and was again centrifuged for 15 minutes. The supernatant liquid was decanted to afford the product. An optical micrograph of the product, taken at 100×, is shown in FIG. 4.

Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

We claim:

1. A method of making a chromonic particle dispersion comprising:
   (a) providing an aqueous mixture comprising (i) a continuous water-soluble polymer phase comprising a water-soluble polymer and (ii) a discontinuous chromonic phase comprising a chromonic material;
   (b) mixing the chromonic material with a multivalent cation salt so as to non-covalently crosslink the chromonic material and form non-covalently crosslinked chromonic particles.

2. The method of claim 1 wherein the non-covalently crosslinked chromonic particles are chromonic nanoparticles having an average particle size of less than 1000 nanometers.

3. The method of claim 1 further comprising:
   contacting the non-covalently crosslinked chromonic particles with a surface modifying agent, selected from an organic oxyacid of carbon, sulfur, phosphorus and combinations thereof, so as to provide surface-modified chromonic particles that are more hydrophilic, hydrophobic, biocompatible, or bioactive than the non-covalently crosslinked chromonic particles.

4. The method of claim 1 wherein the aqueous mixture is prepared by combining an aqueous solution of water soluble polymer and a neutralized aqueous solution of chromonic material.

5. The method of claim 2 wherein the aqueous mixture is added to an aqueous solution of the multivalent cationic salt.

6. The method of claim 4 wherein the neutralized aqueous solution of chromonic material is prepared by treating a chromonic material with an alkali- or alkaline earth metal hydroxide or carbonate.

7. The method of claim 1 wherein the weight ratio of the water soluble polymer to the chromonic material is from 5:1 to 99:1.

8. The method of claim 1 wherein the weight ratio of the water soluble polymer to the chromonic material is from 5:1 to 15:1.

9. The method of claim 1 wherein the concentration of the water-soluble polymer is from 15 to 25 wt.% of the aqueous mixture.

10. The method of claim 1 wherein the concentration of chromonic material is from 0.25 to 7 wt.% of the aqueous mixture.

11. The method of claim 1 wherein the chromonic material is selected from one or more of the following general formulae:

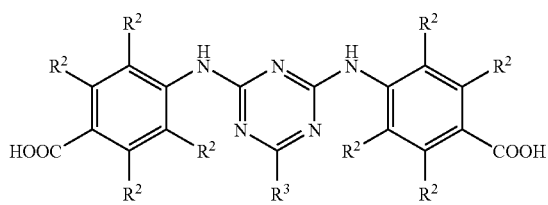

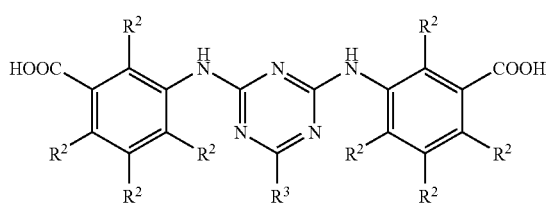

wherein
each $R^2$ is independently selected from the group consisting of electron donating groups, electron withdrawing groups, and electron neutral groups, and
$R^3$ is selected from the group consisting of substituted and unsubstituted heteroaromatic rings and substituted and unsubstituted heterocyclic rings, the rings being linked to the triazine group through a nitrogen atom within the ring of $R^3$,
and zwitterions, proton tautomers, and salts thereof.

12. The method of claim 11 wherein the chromonic material is selected from one or more of the following general formulae:

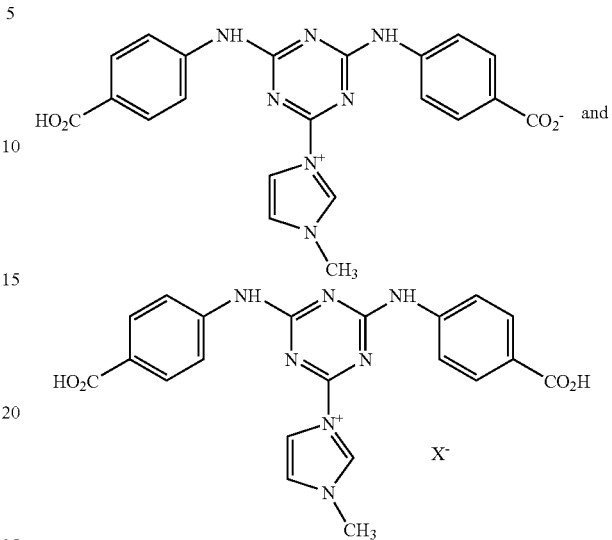

wherein $X^-$ is a counterion.

13. The method of claim 1 wherein the aqueous mixture further comprises a noble metal salt or guest molecule.

14. The method of claim 13 wherein the noble metal salt or guest molecule is contained in the non-covalently crosslinked chromonic particles.

15. The method of claim 14 wherein the non-covalently crosslinked chromonic particles contain the noble metal salt, with said method further comprising:
reducing the contained noble metal salt to an elemental noble metal so as to produce a suspension of elemental noble metal nanoparticles in the non-covalently crosslinked chromonic particles.

16. The method of claim 15 further comprising:
contacting the non-covalently crosslinked chromonic particles with an aqueous solution of a monovalent metal salt so as to reverse the crosslinking and release the contained elemental noble metal nanoparticles.

17. The method of claim 14 wherein the non-covalently crosslinked chromonic particles containing a noble metal salt qre coated onto a substrate.

18. The method of claim 17 further comprising:
reducing the noble metal salt to produce a coated substrate comprising a continuous coating of water-soluble polymer and a discontinuous coating of elemental noble metal particles contained in the chromonic particles.

19. The method of claim 14 wherein the non-covalently crosslinked chromonic particles contain the guest molecule, with said method further comprising removing the water-soluble polymer.

20. The method of claim 3 wherein said contacting comprises isolating the non-covalently crosslinked chromonic particles from the water-soluble polymer, and then suspending the non-covalently crosslinked chromonic particles in a solution of the surface modifying agent.

21. The method of claim 3 wherein surface groups are present on the surface of the surface-modified chromonic particles in an amount such that the surface-modified chromonic particles are capable of being subsequently dispersed in the continuous water-soluble polymer phase without aggregation.

22. The method of claim 21 wherein the surface groups are present in the form of a monolayer on the surface of the surface-modified chromonic particles.

23. The method of claim 3 wherein the surface-modifying agent is selected from organic oxyacids of carbon, sulfur, phosphorus and combinations thereof.

24. The method of claim 13 wherein the aqueous mixture further comprises the guest molecule and an alkaline compound.

25. The method of claim 14 wherein the non-covalently crosslinked chromonic particles contain the guest molecule.

26. The method of claim 25 wherein the quest molecule is selected from dyes, cosmetic agents, fragrances, flavoring agents, and bioactive compounds.

27. The method of claim 26 wherein the guest molecule is a drug.

28. The method of claim 1 wherein the non-covalently crosslinked chromonic particles are larger than 1000 nanometers in size.

29. The method of claim 1 wherein the non-covalently crosslinked chromonic particles are dissolvable in an aqueous solution of univalent cations or other non-ionic compounds.

30. The method of claim 29 further comprising:
adjusting the rate at which the non-covalently crosslinked chromonic particles are so dissolvable by adjusting the type and amount of multivalent cation used for crosslinking.

* * * * *

UNITED STATES PATENT AND TRADEMARK OFFICE
CERTIFICATE OF CORRECTION

PATENT NO. : 7,629,027 B2
APPLICATION NO. : 11/250290
DATED : December 8, 2009
INVENTOR(S) : Moran et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1090 days.

Signed and Sealed this

Second Day of November, 2010

David J. Kappos
*Director of the United States Patent and Trademark Office*

UNITED STATES PATENT AND TRADEMARK OFFICE
CERTIFICATE OF CORRECTION

PATENT NO.        : 7,629,027 B2
APPLICATION NO.   : 11/250290
DATED             : December 8, 2009
INVENTOR(S)       : Cristin E Moran It is certified that error appears in the above-identified patent and that said Letters Patent is hereby corrected as shown below:

On Title Page 2, Col. 1 Item [56]; (Other Publications), Line 3
Delete "Layes:" and insert -- Layer: --, therefor.

Column 4
Line 14 (Approx.), Delete "hexaaryltryphenylene." and insert
-- hexaaryltriphenylene. --, therefor.

Column 5
Line 11, Delete "substituent-" and insert -- substituent --, therefor.

Lines 57-63,

Delete " 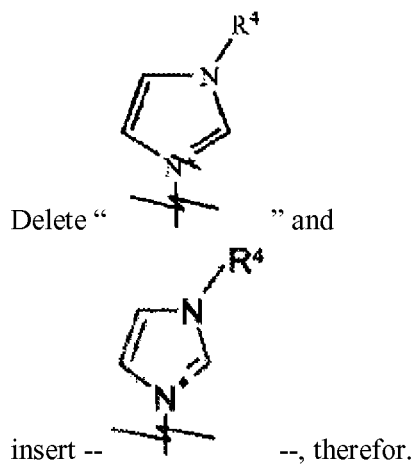 " and insert --  --, therefor.

Column 7
Line 23, Delete "naoparticle." and insert -- nanoparticle. --, therefor.
Line 29, Delete "-the" and insert -- the --, therefor.

Signed and Sealed this
Eleventh Day of September, 2012

David J. Kappos
*Director of the United States Patent and Trademark Office*

CERTIFICATE OF CORRECTION (continued)
U.S. Pat. No. 7,629,027 B2

Column 9
Line 23, Delete "diesters" and insert -- di-esters --, therefor.
Line 23, Delete "dioleyl" and insert -- dioleoyl --, therefor.

Column 10
Line 8, Delete "methods-to" and insert -- methods to --, therefor.

Column 11
Line 30, Delete "ordinarily-unstable" and insert -- ordinarily unstable --, therefor.
Line 31, Delete "formulated-into" and insert -- formulated into --, therefor.

Column 15
Line 61, Delete "I" and insert -- 1 --, therefor.

Column 16
Line 50, Delete "HCI" and insert -- HCl --, therefor.

Column 17
Line 8 (Approx.), Delete "HCI." and insert -- HCl. --, therefor.
Line 12 (Approx.), Delete "HCI." and insert -- HCl. --, therefor.

Column 21
Line 13 (Approx.), In Claim 26, delete "quest" and insert -- guest --, therefor.